United States Patent
Wallace et al.

(10) Patent No.: US 6,920,396 B1
(45) Date of Patent: Jul. 19, 2005

(54) SYSTEM AND METHOD FOR PROVIDING FLEXIBLE ACCESS AND RETRIEVAL OF SEQUENCE DATA FROM A PLURALITY OF BIOLOGICAL DATA REPOSITORIES

(75) Inventors: James C. Wallace, Seattle, WA (US); Kai Wang, Bellevue, WA (US); John Jay Liljeberg, Mill Creek, WA (US)

(73) Assignee: PhenoGenomics Corporation, Bellevue, WA (US)

( * ) Notice: Subject to any disclaimer, the term of this patent is extended or adjusted under 35 U.S.C. 154(b) by 524 days.

(21) Appl. No.: 09/960,877

(22) Filed: Sep. 20, 2001

(51) Int. Cl.[7] .............................................. G06F 17/00
(52) U.S. Cl. ......................................... 702/19; 702/20
(58) Field of Search ..................................... 702/19, 20

(56) References Cited

PUBLICATIONS

MPSRCH Suite of Database Searching Programs, Version 2.0, User/Reference Manual (IntelliGenetics, Inc. 1994).*
"Oracle 9i Application Server," A Technical White Paper [online], Nov. 2000 [retrieved on Jun. 17, 2003] Retrieved from the Internet:<URL: http://technet.oracle.com/products/ias/pdf/9ias_102.pdf>.
"Oracle 9i Application Server," Overview Guide, Release 1.0.2. [online], Nov. 2000 [retrieved on Nov. 12, 2003]. Retrieved from the Internet:<URL: http;//downoad.oracle.com/docs/cds/a97335_01.zip>.
Stabenau, Arne et al., "A guided Tour of Ensembl," European Bioinformatics Institute, 2001, www.ensemble.orgl.
Altschul, Stephan, "Blast Overview," 2001, www.ensemble.orgl.

* cited by examiner

*Primary Examiner*—James Martinell
(74) *Attorney, Agent, or Firm*—Patrick J.S. Inouye

(57) ABSTRACT

A system and method for providing flexible access and retrieval of sequence data from a plurality of biological data repositories is described. A plurality of biological data repositories are maintained. Each data repository contains sequence data stored into structured records uniquely identified. Each data repository is interfaced through a queue handler dynamically locating and selecting at least one such biological data repository and launching a search query against each selected biological data repository. Search query parameters are accepted from a user specifying a search request for a sequence set. Results obtained from a search engine are presented as ordered tables of search results.

63 Claims, 15 Drawing Sheets

Figure 16 (con'd).
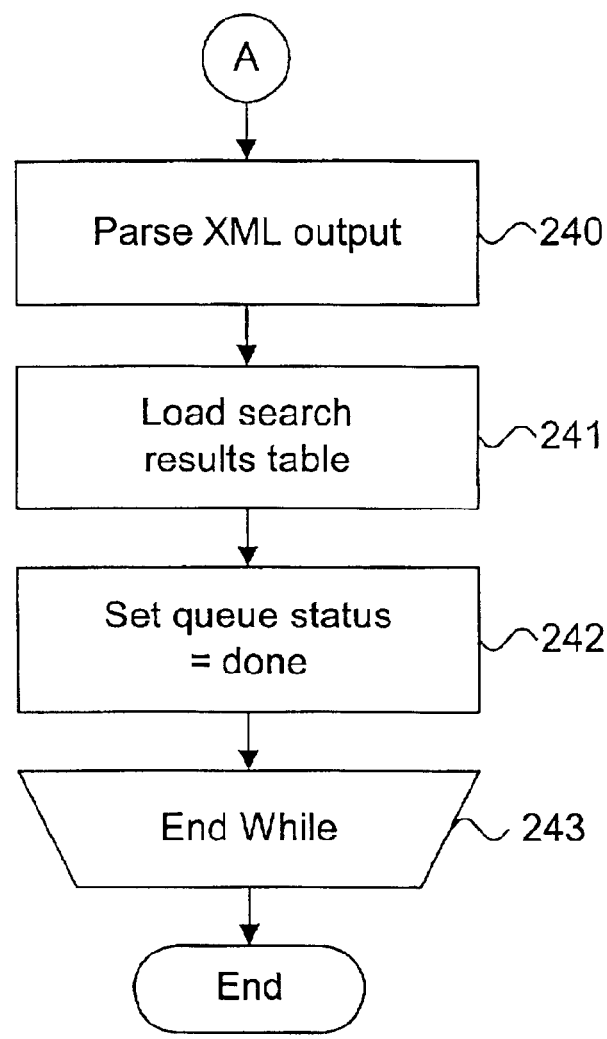

SYSTEM AND METHOD FOR PROVIDING FLEXIBLE ACCESS AND RETRIEVAL OF SEQUENCE DATA FROM A PLURALITY OF BIOLOGICAL DATA REPOSITORIES

FIELD OF THE INVENTION

The present invention relates in general to plurality of biological data repositories access and retrieval and, in particular, to a system and method for providing flexible access and retrieval of sequence data from a plurality of biological data repositories.

BACKGROUND OF THE INVENTION

In the field of bioinformatics, biological data repositories (databases) are used to store sequences of genome information for DNA and protein sequences. Each sequence is a series of capital letters and numerals uniquely identifying a genetic code for DNA nucleotides and amino acids. Internally, each sequence is formed as a structured string organized into primary, secondary, tertiary, and so forth, sets of cloning vectors that can be lengthy and complex.

Worldwide, all known genome sequences are identified and cataloged in three principal public databases. The databases include the GenBank, maintained by the National Center for Biotechnology Information (NCBI); the European Molecular Biology Laboratory (EMBL); and the DNA DataBank of Japan (DDBJ). Each day, the genome sequences maintained in these databases are downloaded and synchronized to provide an up-to-date and consistent repository of collective biological data.

Biological data repositories, such as GenBank, EMBL and DDBJ, are searched on a regular basis as an aid to biotechnical research. As publicly-accessible biological data repositories, each of these databases processes a high volume of queries each day. For example, the GenBank contains over 12 million entries totaling nearly 13 billion base pairs of sequence sets, and receives over 800,000 queries per day from over 120,000 individuals worldwide. The demand for searching availability often exceeds database capacities.

Nevertheless, searching remains a crucial part of on-going research for several reasons. First, individual sequences must be matched and identified, where feasible, to existing DNA and protein sequences to determine the potential characteristics and compositions. Second, identifying a given sequence allows the generation of a probability function predicting behavior and interaction characteristics. Third, biological data repository searching allows the determination of whether a given sequence is novel and, if so, whether the sequence has been the subject of patent or similar protection.

To accommodate the large demand for these public databases, access by each individual user is limited to a fixed maximum number of queries per day. Accordingly, the tools available for accessing these databases have evolved to maximize the limited availability afforded to each user. In particular, with the growth and widespread availability of local and wide area networks, including the Internet, browser-based tools via the World Wide Web (Web) have become available and have significantly displaced older command line-based query tools.

One limitation imposed, in part, by the limited access afforded to public biological data repositories is the disincentivizing of searching multiple sequence sets against one or more of the databases as a single transaction. Rather, each sequence in a set of multiple sequences must be submitted to separate databases as an individual query in serial fashion, one-at-a-time. Furthermore, combined genome sequences must be categorized based on the type of sequence presented, that is, DNA or protein. Single query limitations and type categorizations increase the difficulty attendant to using the public databases.

To alleviate these access constraints, individual users often download and mirror public databases onto a local host for increased search efficiency without the restrictions mandated by the public repositories. However, the same tools used to search local database copies are used on the public repositories and thus provide limited relief from the access restrictions. For instance, these tools lack the necessary mechanisms to process queries for multiple sequences, including mixed sequences containing DNA and protein. These tools also lack the capabilities to process search results on a sequence-by-sequence basis. Other shortcomings exist.

In the prior art, two principal tools for accessing public biological data repositories exist. First, the Ensemble query tool, licensed by EMBL, operates as a browser-based solution for searching one database, one query at a time. The tool directly interfaces to the database engine and operates in a strict request-response manner without intermediate flow control. Sequence results cannot be exported nor can a new database be created based on search results. Control is limited to a serial searching of a single data repository and the results received therefrom are presented for only one sequence request.

Second, the Blast software suite, licensed by NCBI, offers a similar browser-based query tool, but includes a conventional command line interface. Queries can be executed against multiple databases for a single sequence by using the command line interface. However, the user interface is awkward, complex and non-intuitive and requires a high level of expertise to interpret and apply the appropriate flags and parameters as a single command line. As well, both the browser-based and command line interfaces fail to offer any type of meaningful flow control other than a simple serialization of individual queries.

Therefore, there is a need for an approach to providing a capability to search multiple biological data repositories, including public databases, for multiple sequences of biological data for a set of one or more sequences. Preferably, such an approach would provide both pre-processing of queries and post-processing of search results.

There is a further need for providing an intuitive and user-friendly interface to searching data repositories of biological data. Preferably, such an approach would provide a graphical user interface that includes the capability to display substantially unlimited search results sets as generated by a multi-sequence query against multiple databases.

There is a further need for an approach to providing control over the intermediate layer transaction processing of a search query executed against multiple data repositories. Preferably, such an approach would offer load balancing, processing of partial results, and detection of expired searches.

SUMMARY OF THE INVENTION

The present invention provides a system and method for receiving and executing arbitrarily complex searches of biological data repositories for one or more sets of genome sequences. A browser-based user interface provided a front end layer for processing search requests and presenting completed search results in an intuitive and user-friendly format. An intermediate set of processing modules, known as servlets, process the search requests and coordinate queries with a database engine. A queue handler executes independently but in coordination with the servlets to monitor the progress and process the results of the search requests. Summary and detailed search results are presented in an organized, preferably tabular, format on the browser-based user interface.

An embodiment of the present invention provides a system and method for transacting a multi-sequence search against a biological data repository. A set of search query parameters specifying a plurality of sequence sets are received. Each sequence set encodes structured biological data values. A search queue is loaded with the search query parameters formatted into a structured database query for each sequence set assigned by search type. A search of the biological data repository is launched for each sequence set. Search results generated responsive to each such structured database query search are retrieved. The search results are forwarded as sequence set information organized and reformatted for each sequence set and search type.

A further embodiment provides a system and method for accessing a plurality of biological data repositories using an extensible database access framework. Search query parameters are accepted for and search results displayed from a search request for multiple sequence sets performed against a plurality of biological data repositories in a user interface layer. The search request and the search results are processed in an intermediate layer. The user interface layer is interfaced by processing the search query parameters into a structured database query and presenting database results as the formatted search results. The structured database query is executed in a database layer. At least one queue handler loading the structured database query is provided. A plurality of biological data repositories are selected. The database results are retrieved. Each biological data repository contains sequence data stored into unstructured records which are each identified by a unique identifier. The structured database query is executed against at least one database engine. The database results are obtained from the selected biological data repositories.

A further embodiment provides a system and method for providing flexible access and retrieval of sequence data from a plurality of biological data repositories. A plurality of biological data repositories are maintained. Each data repository contains sequence data stored into structured records uniquely identified. Each data repository is interfaced through a queue handler dynamically locating and selecting at least one such biological data repository and launching a search query against each selected biological data repository. Search query parameters are accepted from a user specifying a search request for a sequence set. Results obtained from a search engine are presented as ordered tables of search results.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 4 is a screenshot showing, by way of example, a Web page for accepting a description of a new search.

DETAILED DESCRIPTION

Figure 1:
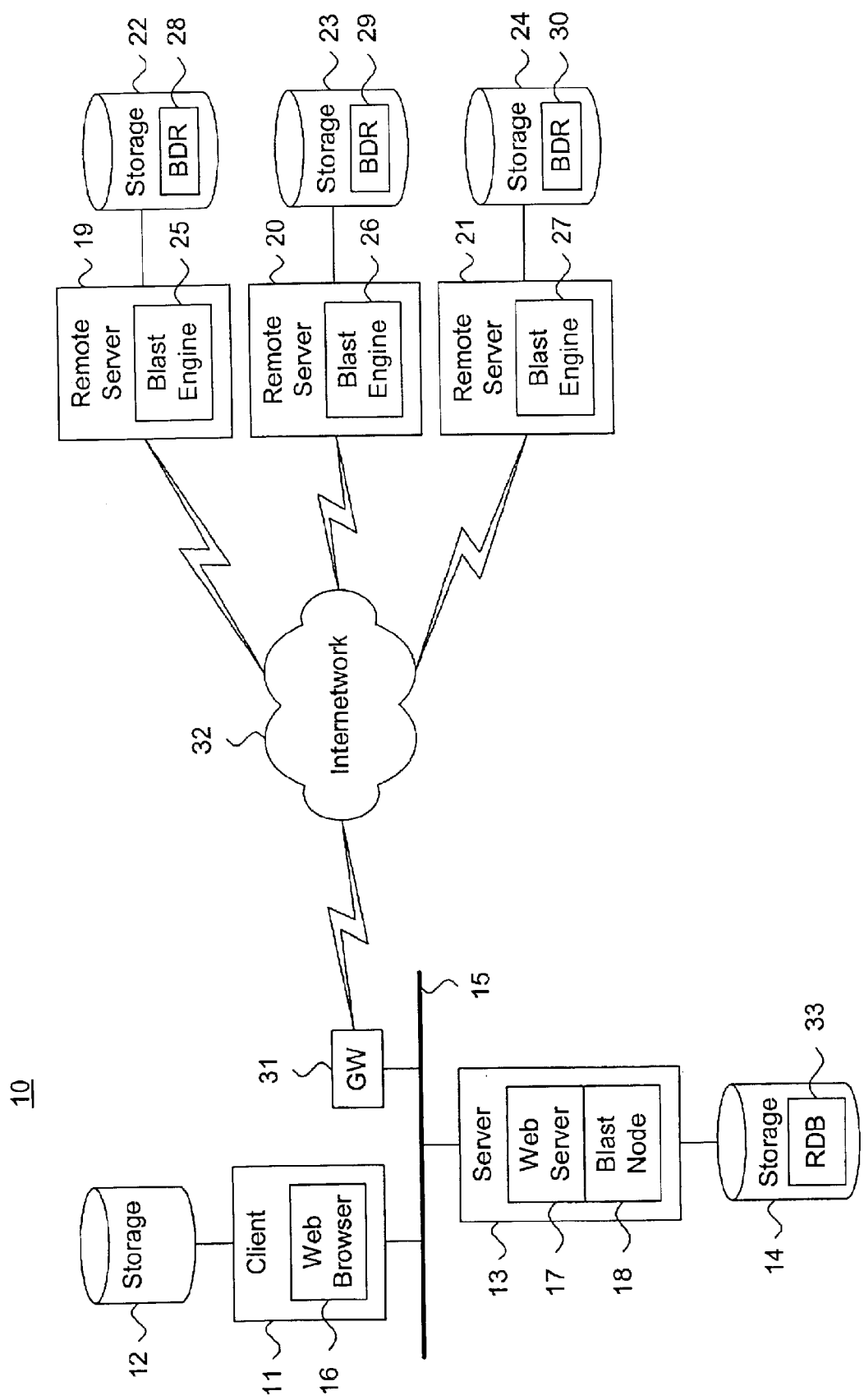
FIG. 1 is a functional block diagram showing a distributed computing environment, including a system for providing flexible access and retrieval of sequence data from a plurality of biological data repositories, in accordance with the present invention.

FIG. 1 is a functional block diagram showing a distributed computing environment 10, including a system for providing flexible access and retrieval of sequence data from a plurality of biological data repositories (BDRs) 28–30, in accordance with the present invention. A client 11 executes a Web browser 16 to request and receive content from a Web server 17 executing on a server 13 interconnected via a data network. Locally, the client 11 is interfaced to the server 13 via an intranetwork 15, but could be alternatively interfaced to an external server (not shown) via an internetwork 32, including the Internet, through a gateway 31 or similar broadband network routing device. The client 11 includes a storage device 12 for maintaining a file system persistently storing application and data files.

The server 13 executes the Web server 17 and a Blast Node 18 which functions as an intelligent queue handler, as further described below with reference to FIG. 2. The server 13 also includes a storage device 14 for maintaining a file system persistently storing application and data files, including a relational database (RDB) 33. The relational database 33 stores tables and queues relating to search requests and results as transacted by the Blast Node 18.

The Web server 17 and Blast Node 18 together process sequence searches executed against the biological data repositories 28–30. The Web server 17 interfaces to each individual client 11 via a Web browser 16 which provides a graphical and intuitive user interface to individual users. The Blast Node 18 submits searches to Blast (database) engines 25–27 respectively executing on one or more remote servers 19–21 interconnected via the internetwork 32. Each remote server 19–21 also includes a storage device 22–24 for maintaining a file system persistently storing application and data files, including the biological data repositories 28–30. Other network configurations and topologies and arrangements of clients, local and remote servers, storage devices, and biological data repositories and relational databases are feasible, as would be recognized by one skilled in the art.

In the described embodiment, the individual client 11 is a personal computer system (or cluster of personal computer systems) capable of running a standard HTML-compatible Web browser, such as Windows, Linux or Solaris. The Web browser 16 is a standalone Web browser, such as the Internet Explorer, licensed by Microsoft Corporation, Redmond, Wash., or the Navigator, licensed by Netscape Corporation, Santa Clara, Calif. The relational database 33 is an Oracle-compatible database, such as licensed by Oracle Corporation, Redwood Shores, Calif.; the Apache Tomcat Webserver servlet engine, licensed by The Apache Software Foundation, Forest Hill, Md.; the Java Runtime Environment (JRE), licensed by Sun Microsystems, Inc., Palo Alto, Calif.; and the Blast Program Suite, licensed by the NCBI.

Figure 2:
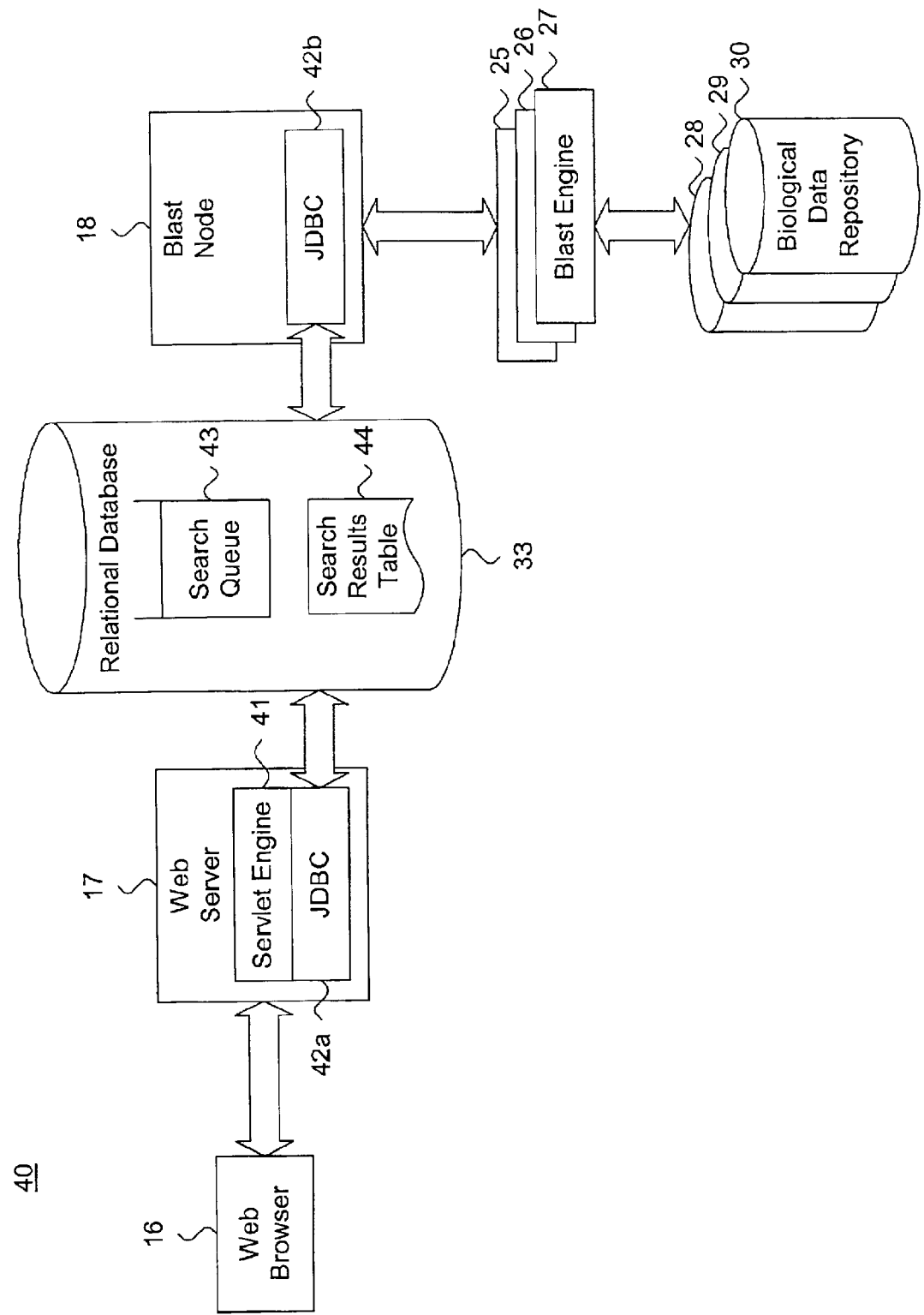
FIG. 2 is a block diagram showing the system for providing flexible access and retrieval of sequence data of FIG. 1.

FIG. 2 is a block diagram showing the system 40 for providing flexible access and retrieval of sequence data of FIG. 1. The complete system 40 includes the functions performed by the Web browser 16, Web server 17 and Blast node 18. Each of these components could be provided on the same platform, or as could preferably be provided as separate process executing on independent machines to provide coarse or fine grained flow control.

The Web browser 16 provides an intuitive and user-friendly graphical user interface for submitting search queries, monitoring the status of searches, and for receiving summary, graph and detailed search results, as further described below with reference to FIGS. 4, 6, 7, and 8. Through the Web browser 16, search requests for specifying single or multiple sequences against single or multiple biological data repositories 28–30, in various formats, can be entered, as further described below with reference to FIG. 3.

The Web server 17 and Blast node 18 provide an intermediate layer of processing between the Web browser 16 and each of the Blast engines 25–27. The Web server 17 includes a servlet engine 41 that executes server-side applications for providing support to the user interface and database, as further described below with reference to FIG. 3. Individual search requests received from the Web browser 16 are parsed and processed by the servlet engine 41 into formatted database query commands executable by a Blast engine. The formatted search requests are then enqueued into a search queue 43 maintained within the relational database 33. Similarly, search results are retrieved from a search results table 44 also maintained within the relational database 33 and presented to the Web browser 16.

The Blast node 18 functions as an intelligent queue handler that identifies the characteristics of individual search requests irrespective of originating client and dynamically locates and selects an appropriate biological data repository 28–30 against which to execute each search request. The Blast node 18 launches each search against the Blast engine 28–30 corresponding to the selected biological data repository 28–30. Upon detecting the completion (or failure) of a search, the Blast node 18 parses the output from the Blast engine 34 and loads the search results into the search results table 44 in the relational database 33. In the described embodiment, the results from each search request are output from each Blast engine 25–27 as an XML script.

Each Blast engine 25–27 executes Blast-compatible searches and outputs search results in XML format. Each search request must be specified as a formatted and parameterized command line providing input sequences, parameters, and search databases. Each command line is built by the servlets executed by the servlet engine 41 and is submitted to a Blast engine 28–30 by the Blast node 18.

In the described embodiment, both the Web server 17 and Blast node 18 include a Java Database Connectivity (JDBC) module 42a–b for interfacing to the relational database 33. As well, the servlet engine 31 retrieves and executes servlets written in the Java programming language, but could also include Active Server Page (ASP) scripts or similar server-based executables.

Figure 3:
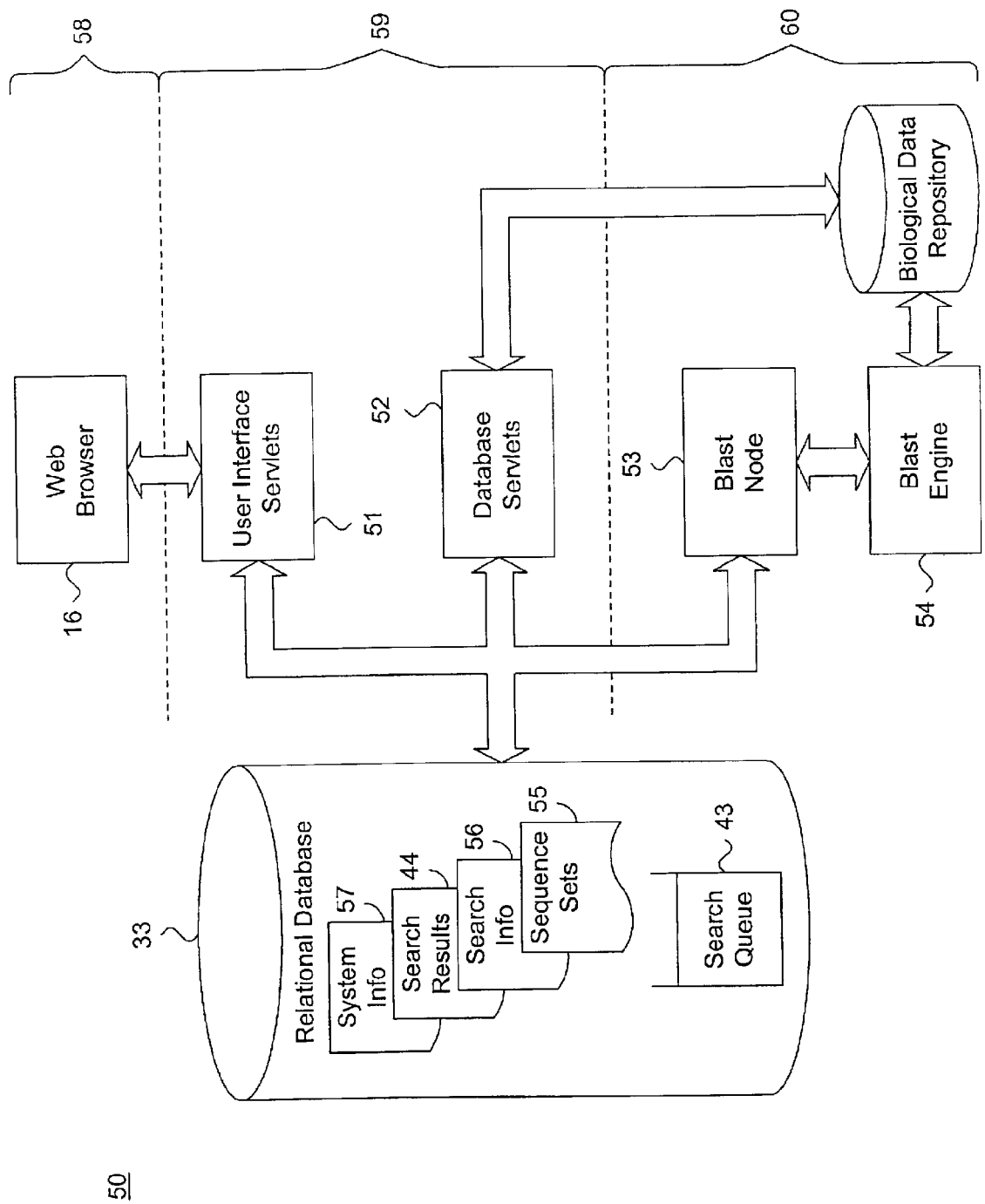
FIG. 3 is a block diagram showing the functional modules of the system for providing flexible access and retrieval of sequence data of FIG. 2.

FIG. 3 is a block diagram showing the software modules of the system 30 for providing flexible access and retrieval of sequence data of FIG. 2. The system 30 is logically architected into three layers: front-end 58, back-end (or intermediate) 59 and Blast (database) 60. In the front-end layer 57, individual Web browsers 16 accept new search queries and present search results in an intuitive and user-friendly browser-based environment. The Web browsers 16 interface to the intermediate layer 59 through the Web server 17 via packets exchanged in compliance with the Hypertext Transport Protocol (HTTP). Alternatively, the Web browsers 16 could interface via an application programming interface or remote procedure call convention, as would be recognized by one skilled in the art.

Each Web browser 16 accepts sequence sets and displays search results, preferably as content generated from HTML scripts. Each client 11 (shown in FIG. 1) includes a communications protocol stack that includes an HTML-compatible protocol layer. As further described and shown below with reference to FIG. 4, a new search can specify new or previously-entered sequence sets, one or more database selections, statistical set information, and various other search descriptive data. As further described and shown below with reference to FIG. 6, a search summary can specify the search results for multiple sequence sets and multiple databases. As further described and shown below with reference to FIG. 7, a search graph can graphically compare search results for multiple sequence sets and multiple databases. Finally, as further described and shown below with reference to FIG. 8, a search detail can specify in separately viewable windows individual sequence information in annotated form accompanied by the query sequence.

In the intermediate layer 59, two groups of servlets 51, 52 interface each Web browser 16 to a Blast engine 54 by way of a Blast node 53. The servlet engine 41 (shown in FIG. 2) executes the servlets 51, 52. The first servlet group, user interface servlets 51, provide server-side support to process incoming search queries received from and to format outgoing search results sent to the Web browsers 16, including:

(1) Staging and queueing user search requests;
(2) Adding, removing and formatting sequence databases;
(3) Importing and exporting DNA and protein sequences from and to external file systems;

(4) Providing systems statuses; and (5) Presenting interactive HTML graphical search results. The user interface servlets 51 parse and process search requests received from each Web browser 16 into formatted database queries in a Blast-compatible command line format. The processed database queries are then placed into the search queue 43 for processing by the Blast node 53.

The second servlet group, database servlets 52, support interaction with the Blast engine 54 by coordinating and executing external Blast engine operations, including:

(1) Creating Blast format databases; and (2) Retrieving sequence entries from Blast-formatted databases. Other groupings of servlets are feasible.

In the described embodiment, the following Java classes are used to provide servlets:

(1) fnew.class: queries database tables and builds Web pages; and (2) bnew.class: uploads sequences, checks compositions, computes search types, loads search queue with search information, and directs Web server to send queue page to user Web browser.

Other Java servlet classes are feasible.

In the database layer 60, a Blast node 53 directly interfaces to the Blast engine 34. The Blast node 53 retrieves individual search requests from the search queue 43 and stores search results into the search results table 44. A Blast engine 54 searches a corresponding biological data repository 61 for the requested sequence sets.

Search requests are launched by users via a Web browser 16, but are actually assigned and sent to a selected Blast engine 54 once the Blast node 53 retrieves the search requests from the search queue 43. Searches therefore occur in an event-based manner. The Blast node 53 interacts with each Blast engine 54, including:

(1) Retrieving queued search requests from the search queue 43;

(2) Running searches on a selected Blast engine 54;

(3) Parsing and loading search results into the search results table 44; and (4) Updating system status.

Although only a single Blast node 53 is necessary for interfacing to one Blast engine 54, multiple Blast nodes 53 can also be utilized, executing either synchronously or asynchronously, on one or more servers 13 to provide control over concurrent database queries and to balance execution of parallelized queries by a plurality of Blast engines 54. Each Blast node 53 would include control logic to prioritize and schedule execution of Blast searches or similar forms of structured database queries.

The user interface servlets 51, database servlets 52 and Blast node 53 interface to the relational database 33 via JDBC modules 42a–b (shown in FIG. 2). In addition to the search queue 43 and search results table 44, the relational database 33 stores a sequence sets table 55, search information table 56 and system information table 57. The sequences sets table 55 is used to store historical data regarding previously-entered sequences. The search information table 56 is used to store statistical and non-sequence search information. Finally, the system information table 57 is used to store client-particular data.

Figure 4:
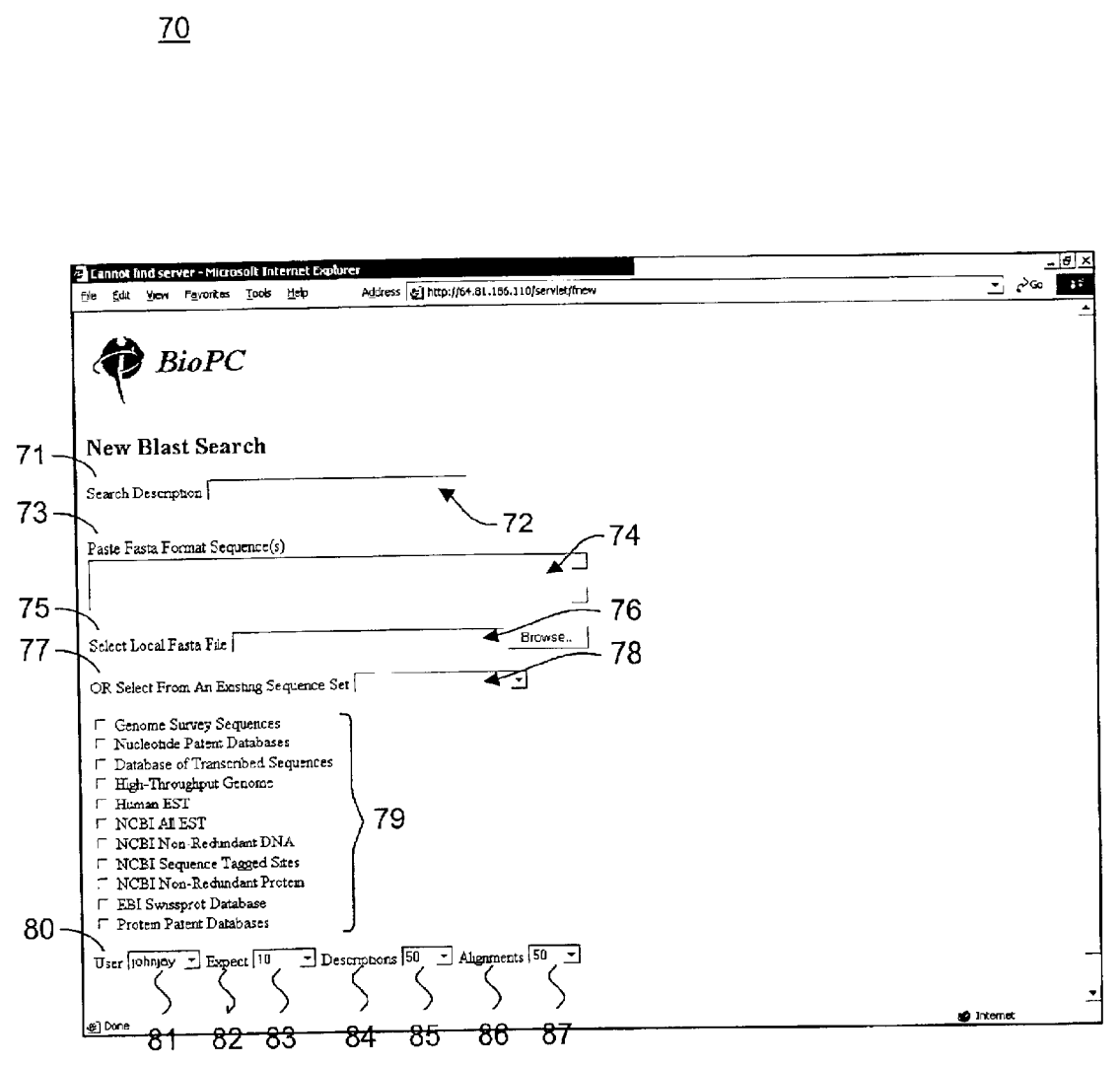

FIG. 4 is a screenshot 70 showing, by way of example, a Web page for accepting a new search. To specify a new biological data search request, the user enters a search description 71 in a search description text box 72, followed by either a new set of FASTA formatted sequences 73 in a formatted sequence set text box 74, a local file 75 in a local file text box 76, or an existing sequence set 77 in an existing sequence set text box 78. In addition, one or more biological data repositories (databases) 79 specifying the appropriate biological data repositories to search are selected. Finally, the user 80 is selected with a user pull-down menu 81, the expected range of search results 82 are selected with an expected search results pull-down menu 83, the range of descriptions 84 is selected with a descriptions pull-down menu 85, and data alignments 86 are selected with a data alignments pull-down menu 87. Finally, the search is submitted by toggling a "Blast search" launch button (not shown). The expected search results range 82 is used during the displaying of summary search results, as further described and shown below with reference to FIG. 7.

Figure 5:
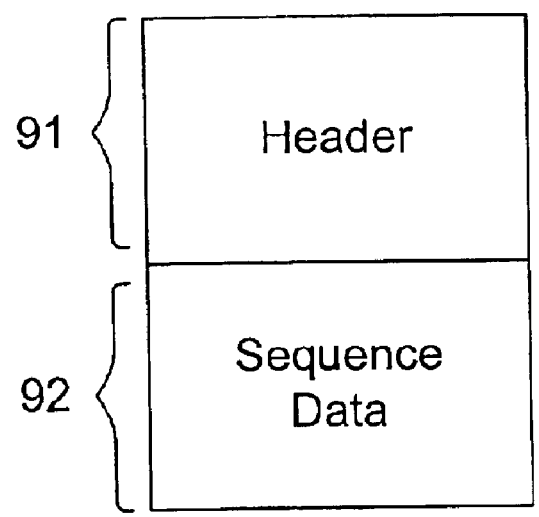
FIG. 5 is a data structure showing a biological data sequence record stored in the database of FIG. 1.

In the described embodiment, each individual search request must be specified in the FASTA sequence data format or as plaintext. FIG. 5 is a data structure showing biological data sequence record 90 stored in the databases 12, 14, 22–24 of FIG. 1. Each individual record 90 includes a header 91 and sequence data 92. The header 91 includes an identifier that uniquely identifies the accompanying sequence data 92.

In the described embodiment, each record conforms to the FASTA format. By way of illustration, an example of a partial DNA sequence in FASTA format for the HIV virus is as follows:

>gi|15209251|emb|AJ291719.1|HIM291719 Human immunodeficiency virus type 1 complete genome, strain 99FR-MP129

Similarly, an example of a protein sequence in FASTA format for the HIV virus is as follows:

>gi|15211841|emb|CAA64159.1| envelope glycoprotein gp120 [Human immunodeficiency virus type 1]

Other forms of sequence record formatting are feasible, as would be recognized by one skilled in the art.

Figure 6:
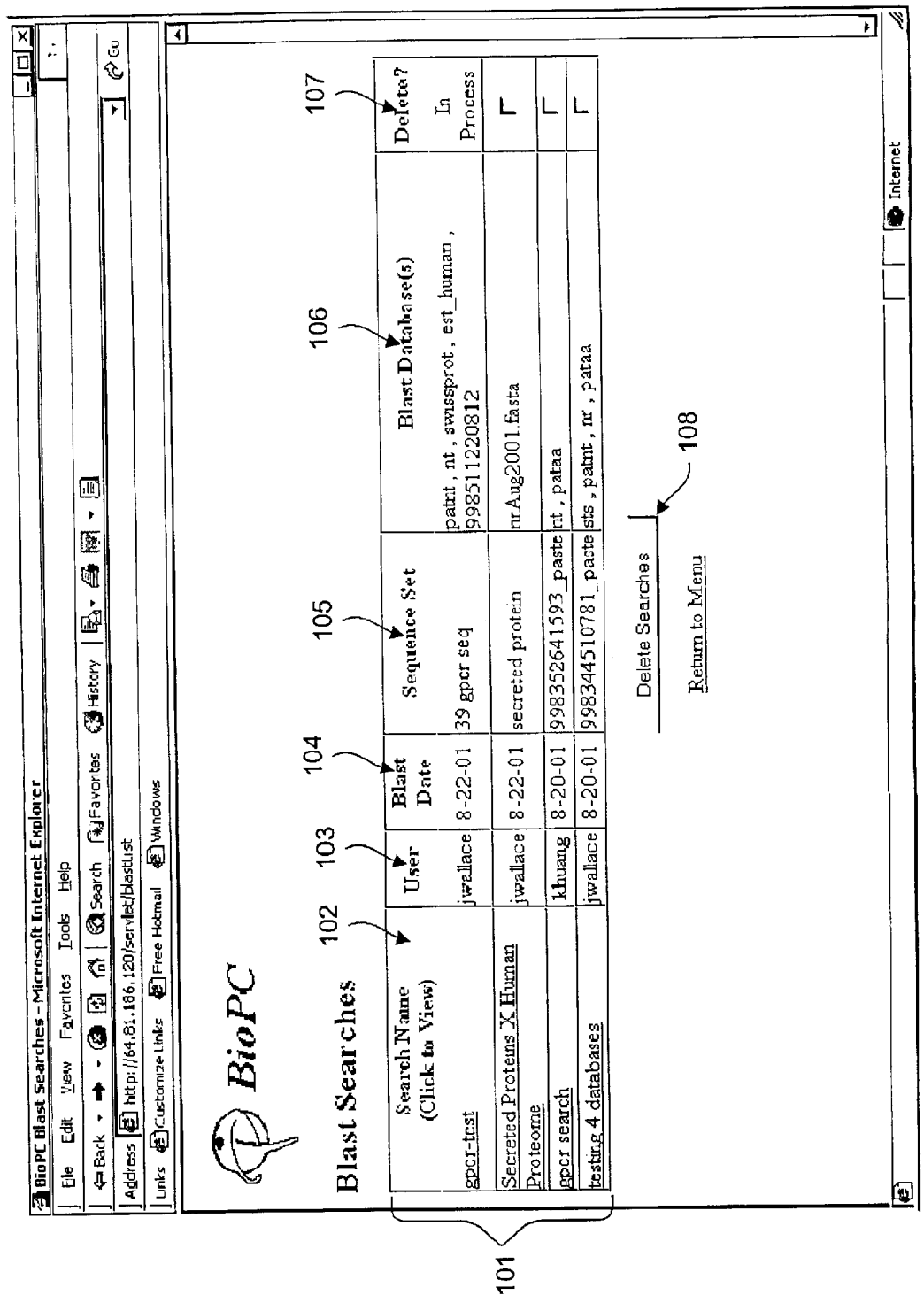
FIG. 6 is a screenshot showing, by way of example, a Web page for displaying a search summary.

FIG. 6 is a screenshot 100 showing, by way of example, a Web page for displaying a search summary. The search summary is presented as a table 101 listing out in columns the search name 102, requested user 103, date 104, sequence set 105, databases 106, and deletion flag 107. The table 101 is necessary to display the individual results based on the specified database and requesting sequence, as each search can include multiple sequences and multiple databases. Individual search results can be deleted by pressing the "Delete Searches" button 108. Detailed search results can be obtained by selecting an appropriate search name 102.

Figure 7:
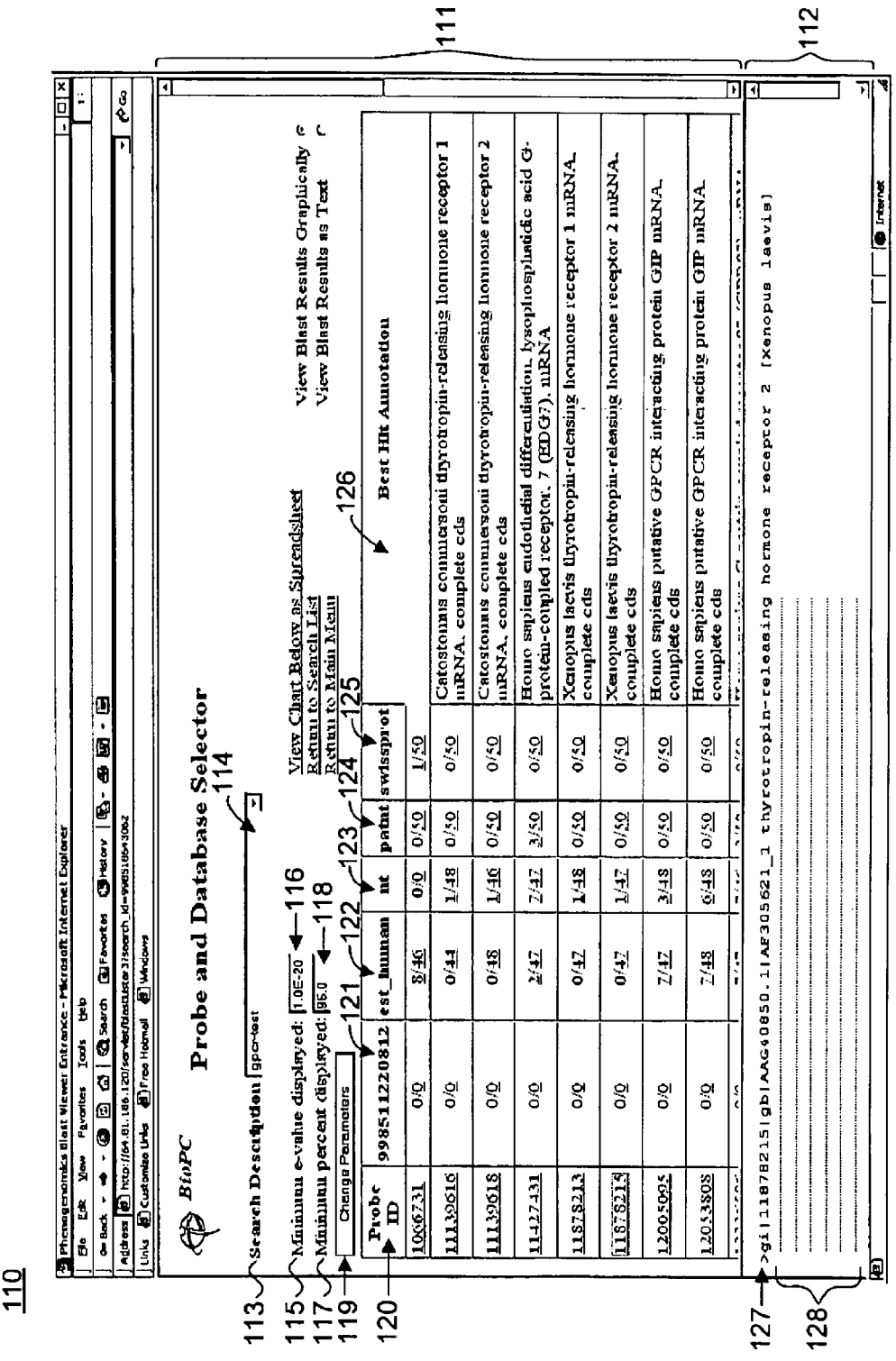
FIG. 7 is a screenshot showing, by way of example, a Web page for displaying search details.

FIG. 7 is a screenshot 110 showing, by way of example, a Web page for displaying search details. The search details are organized into two screen areas. The top screen area 111 shows an individual search description 113 entered when staging a search as selected via the pull-down search description menu 114. The lower screen area 112 indicates the query sequence by header 127 and sequence data 128.

As displayed, the search details satisfy a minimum e-value 115, as entered into an e-value text box 116, and a minimum percent 117, as entered into a minimum percent text box 118. The set of matching search results are presented in a table organized by probe identifier ("Probe ID") 120.

In addition, the table lists actual search result tallies for select databases 121–125, including a user-created database ("998511220812") 121, the NCBI human express sequence database ("est_human") 122, the GenBank non-redundant nucleotide database ("nt") 123, the GenBank patented nucleotide database ("patnt") 124, the EBI protein database ("swissprot") 125, and an annotation for best matching sequence from databases 121–125 ("Best Hit Annotation") 126.

In particular, each of the tallies listed under the databases 121–125 includes a pair of numbers n/m, where n represents the number of subject sequences matched based on the minimum e-value 126 and minimum percent value 128 and m represents the number of subject sequences matched using the criteria set user 81, expected results 83, descriptions 85, and alignments 87 (shown in FIG. 4). Upon selecting one of these tallies, a search graph screen, as shown and described below with reference to FIG. 8, is generated.

Figure 8:
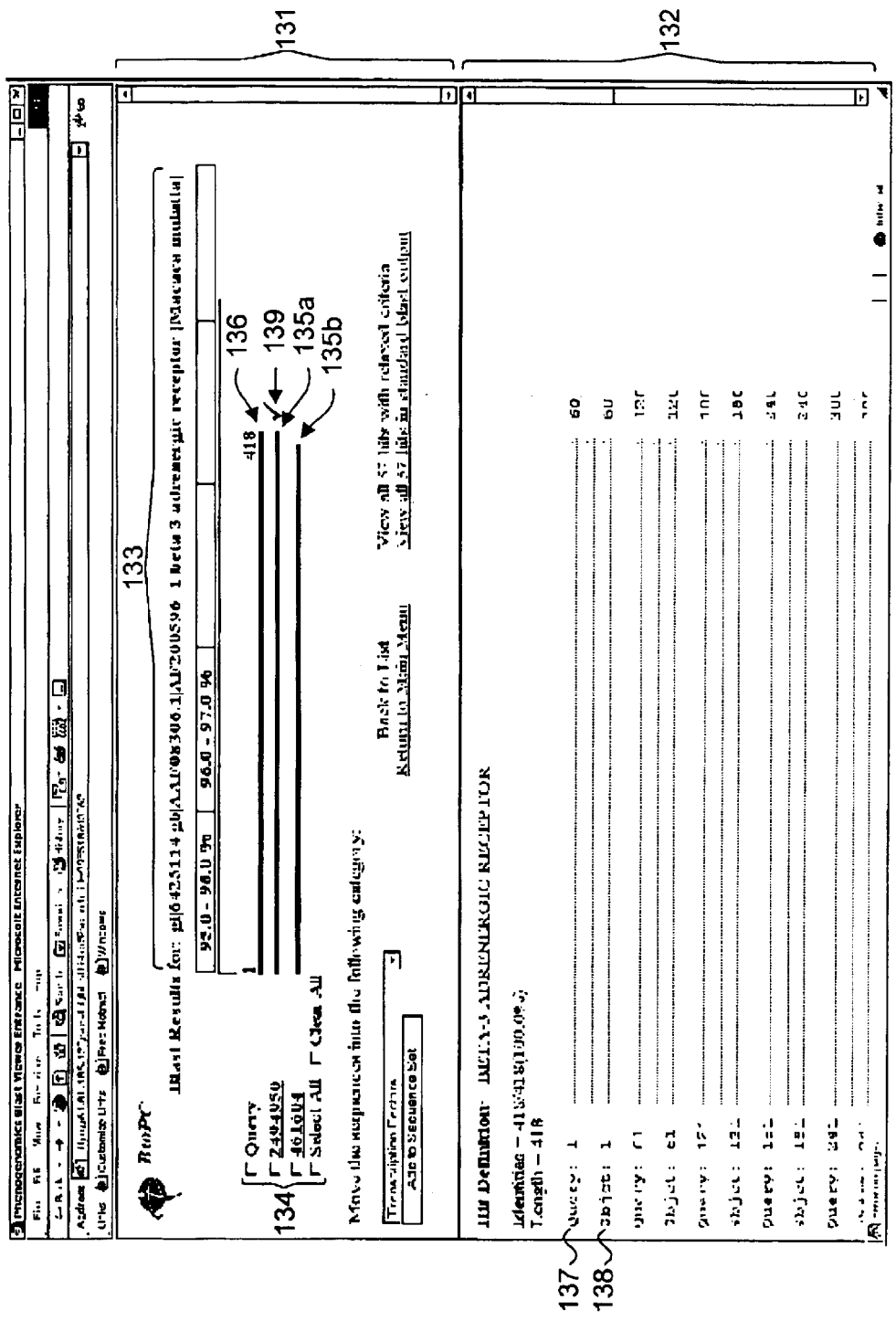
FIG. 8 is a screenshot showing, by way of example, a Web page for displaying a search graph.

FIG. 8 is a screen shot 130 showing, by way of example, a Web page for displaying a search graph. The search graph is organized into two screen areas. The top screen area 131 shows a similarity scale 133 and individual search results 134. Each search result 134 includes a graph of the query sequence 136 and associated graphs 135a–b of search result sequences falling within a set of tallied results (shown in FIG. 7). The lower screen area 132 indicates sequence set alignment between search query 137 and corresponding subject 138 for a selected search result sequence 135a, as indicated by a check mark 139, and the query sequence 136.

Figure 9:
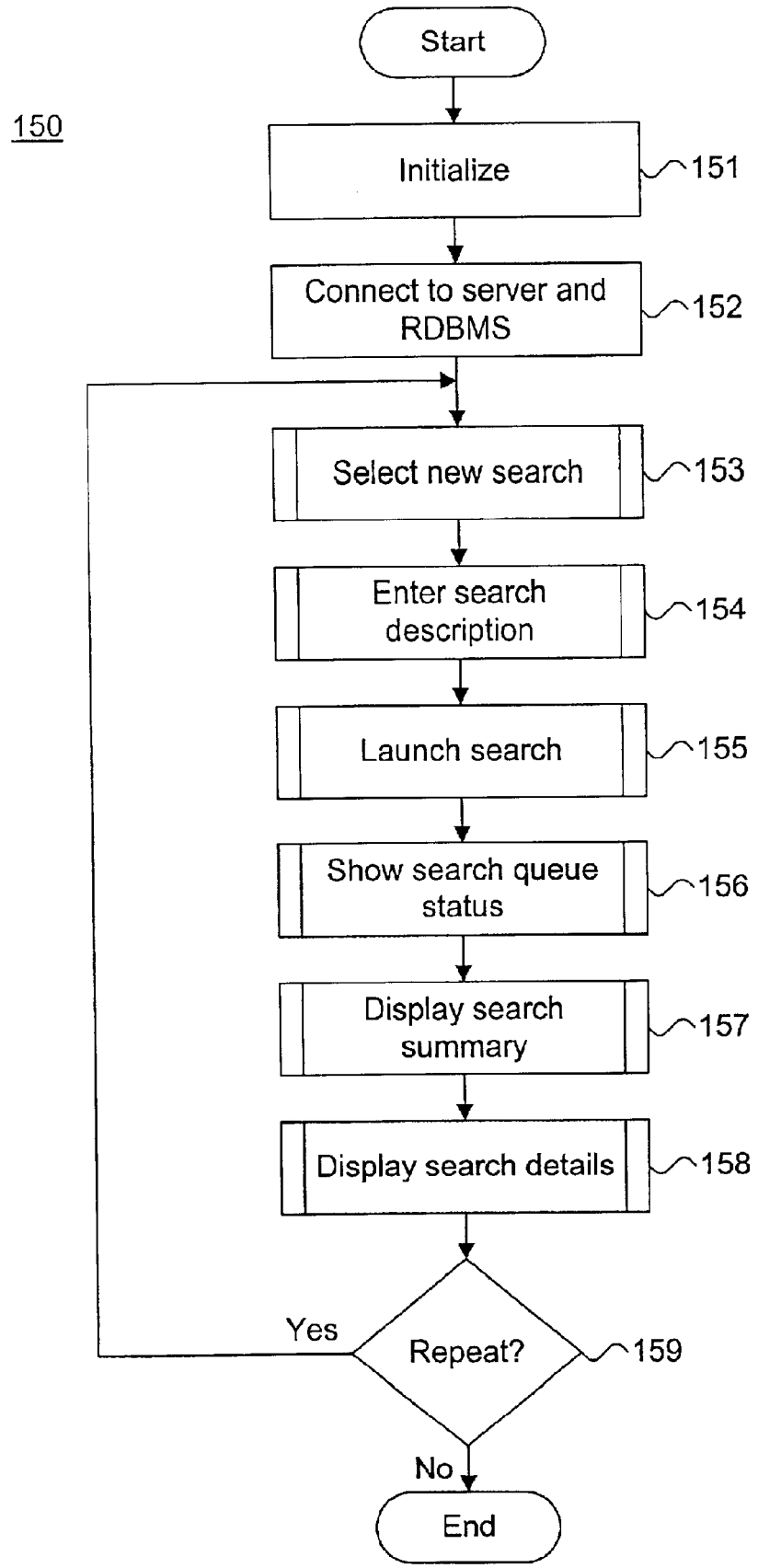
FIG. 9 is a flow diagram showing a method for providing flexible access and retrieval of sequence data from a plurality of biological data repositories in accordance with the present invention.

FIG. 9 is a flow diagram showing a method 150 for providing flexible access and retrieval of sequence data from a plurality of biological data repositories, in accordance with the present invention. The method is described with reference to operations performed via the Web browser 16 for a search performed and executed by the system 30 of FIG. 2.

Thus, the system 30 is initialized (block 151) by requesting and opening a home page in the Web browser 16. The Web browser 16 connects to the server 13 and relational database management system 18 (block 152). Upon the selection of a new search page, a new search is selected (block 153), as further described below with reference to FIG. 10, and via a Web page, such as shown and described above with reference to FIG. 4. A search description is entered (block 154), including the entering of a set of sequences and selecting the appropriate biological data repositories against which to search, as further described below with reference to FIG. 11.

Next, the search is launched (block 155), as further described below with reference to FIG. 12. The launching of the search is actually performed by the Blast node 53 upon receiving a validated search request by querying the search queue 43 in the relational database 33 at regular intervals. The status of the search queue 32 (shown in FIG. 2) is shown (block 156), as further described below with reference to FIG. 13.

Upon the completion of the search or at any time, a search summary can be displayed (block 157) to view search results, as further described below with reference to FIG. 13, and via a Web page, such as shown and described above with reference to FIG. 6. If selected, search details are displayed (block 158), as further described below with reference to FIG. 15, and via a Web page, such as shown and described above with reference to FIG. 8. Additional searches can be submitted and the process is repeated (block 159). Otherwise, the method terminates.

Figure 10:
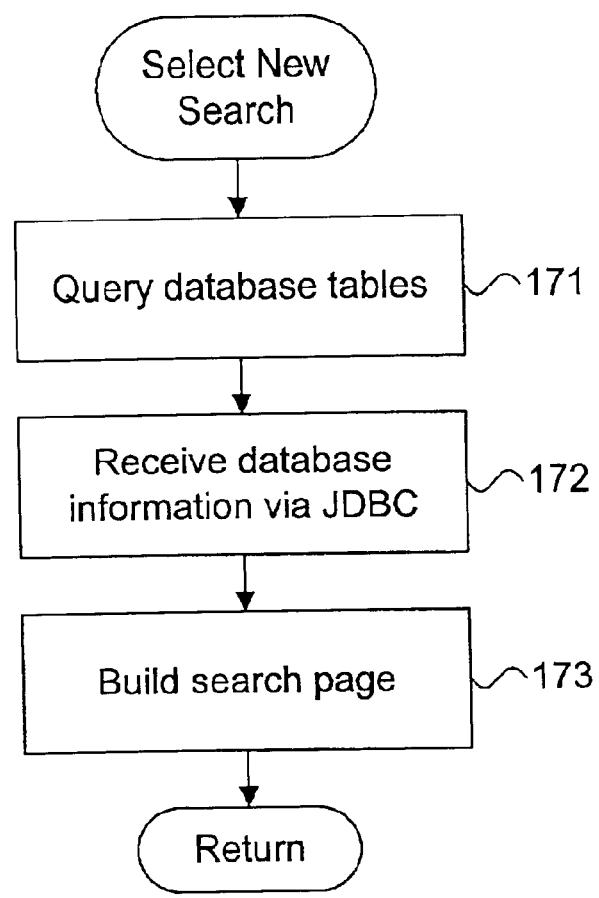
FIG. 10 is a flow diagram showing the routine for selecting a new search for use in the method of FIG. 9.

FIG. 10 is a flow diagram showing the routine 170 for selecting a new search for use in the method 150 of FIG. 9. The purpose of this routine is to execute the intermediate level servlets 51, 52 to query and interface with the databases 35.

Thus, the database tables for system information 54, search information 55, and search results 56 (shown in FIG. 3) are queried (block 171). The requested database information is received via the JDBC module 33 (shown in FIG. 2) (block 172) and a search page is built and served to the Web browser 17 (block 173). The routine then returns.

Figure 11:
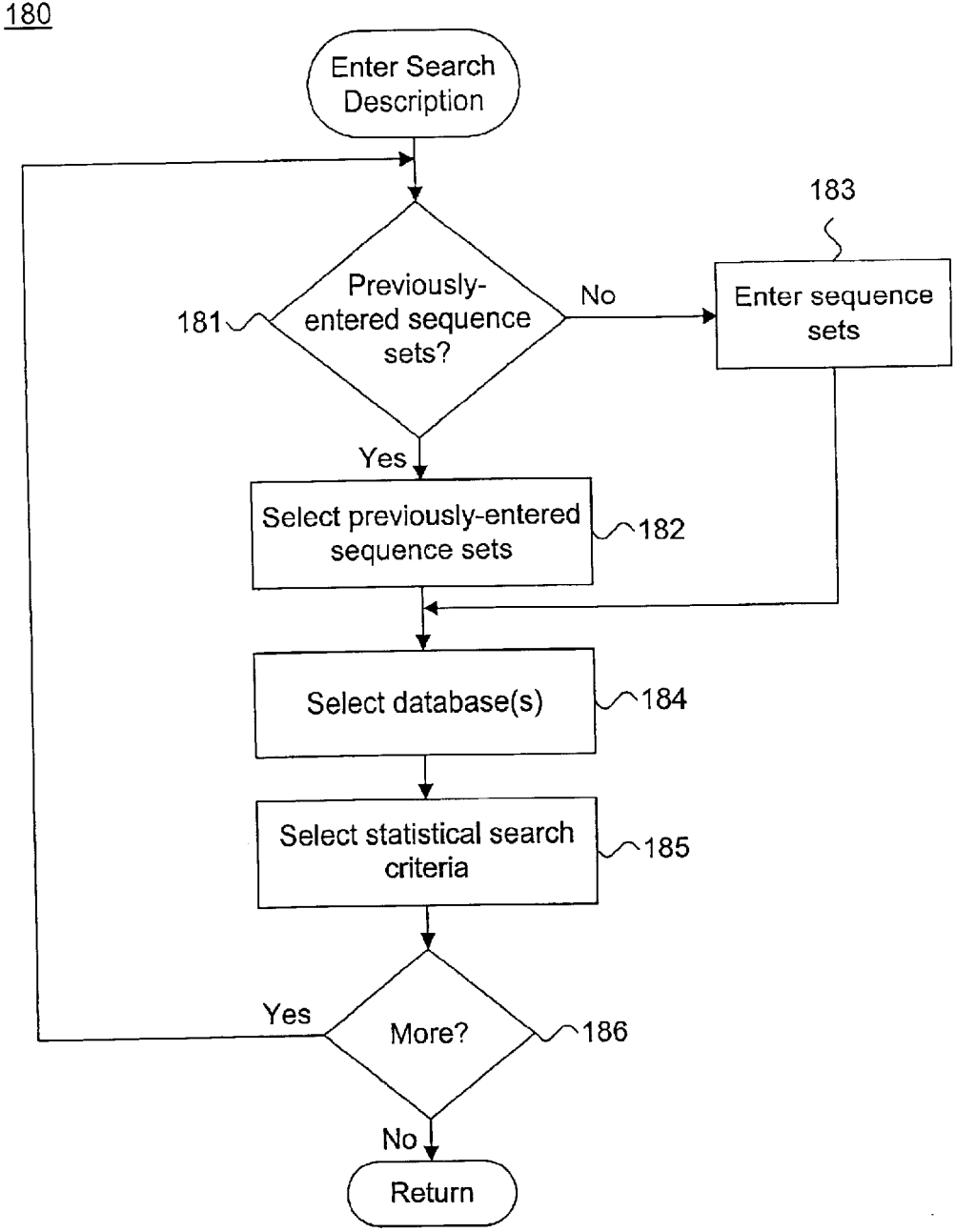
FIG. 11 is a flow diagram showing the routine for entering a search description for use in the method of FIG. 9.

FIG. 11 is a flow diagram showing the routine 180 for entering a search description for use in the method 150 of FIG. 9. The purpose of this routine is to parse through the various fields in the search request Web page, such as shown and described above with reference to FIG. 4.

Thus, if a previously-entered sequence set is being submitted (block 181), the previously-entered sequence sets are selected and entered (block 182). Otherwise, new sequence sets are entered (block 183). The appropriate databases 35 are selected, including the requested biological data repositories and local databases (block 184). The statistical search criteria are selected (block 185). Additional sequence sets, databases, and statistical search criteria can be indicated (block 186). Otherwise, the routine returns.

Figure 12:
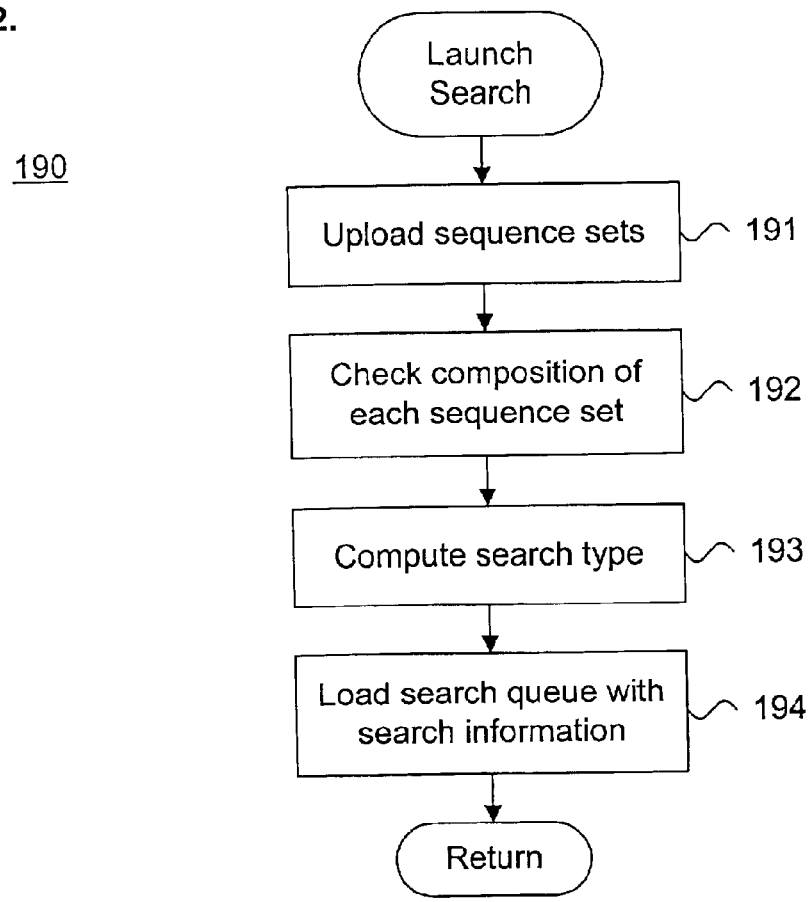
FIG. 12 is a flow diagram showing the routine for launching a search for use in the method of FIG. 9.

FIG. 12 is a flow diagram showing the routine 190 for launching a search for use in the method 150 of FIG. 9. The purpose of this routine is to perform the intermediate layer servlets to upload and submit a validated search queries to the search queue 32 (shown in FIG. 2).

Thus, the sequence sets are uploaded (block 191) from the Web browser 17. The composition of each sequence set is checked (block 192) for the appropriate sequence type, that is, DNA or protein. The search type is computed (block 193) based on the composition of each sequence set. Finally, the search queue 32 is loaded with the search information (block 194). The routine then returns.

Figure 13:
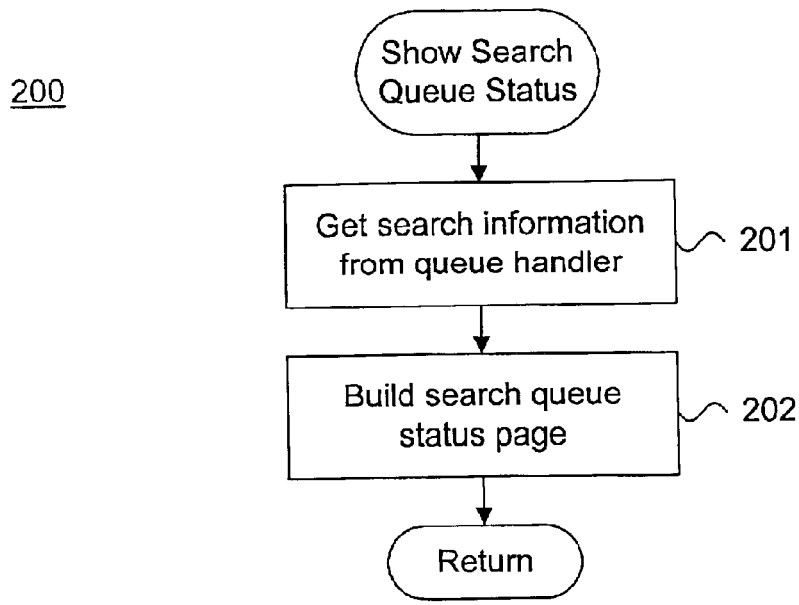
FIG. 13 is a flow diagram showing the routine for showing search queue status for use in the method of FIG. 9.

FIG. 13 is a flow diagram showing the routine 200 for showing the search queue status for use in the method 150 of FIG. 9. The purpose of this routine is to provide an intermediate layer servlet for displaying the status of an ongoing search request on the Web browser 17.

Thus, search information is obtained from the Blast node 53 (shown in FIG. 3) (BLOCK 201). A search queue status page is built (block 202) and served to the Web browser 17. The routine then returns.

Figure 14:
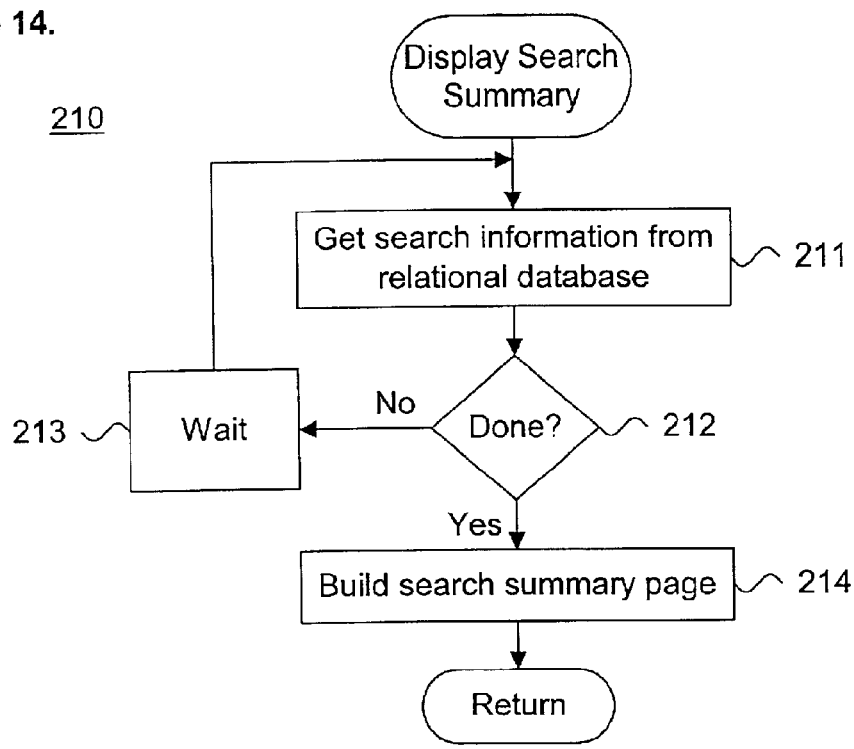
FIG. 14 is a flow diagram showing the routine for displaying a search summary for use in the method of FIG. 9.

FIG. 14 is a flow diagram showing the routine 210 for displaying a search summary for use in the method 150 of FIG. 9. The purpose of this routine is to provide an intermediate layer servlet for displaying a search summary Web page, such as shown and described above with reference to FIG. 6.

Thus, search information 56 (shown in FIG. 3) is obtained from the relational database 33 (block 211). If the search is not done (block 212), the routine waits until the search is complete (block 213). Otherwise, a search summary page is built (block 214) and served to Web browser 17. The routine then returns.

Figure 15:
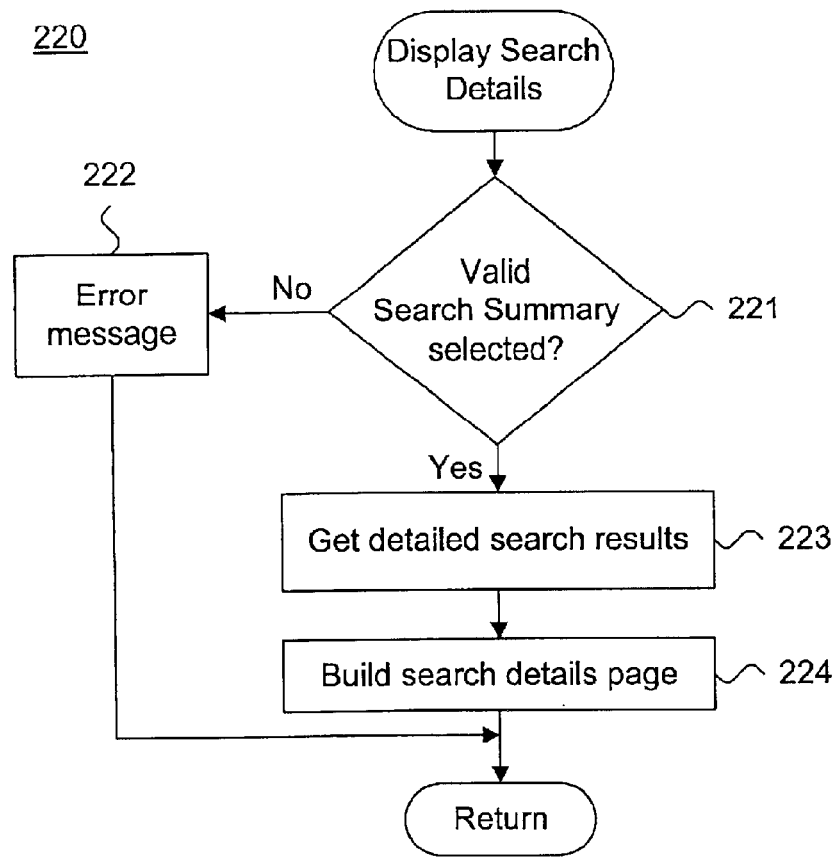
FIG. 15 is a flow diagram displaying search details for use in the method of FIG. 9.

FIG. 15 is a flow diagram displaying search details 220 for use in the method 150 of FIG. 9. The purpose of this routine is to provide an intermediate layer servlet for displaying a selected search details Web page, such as shown and described above with reference to FIG. 8.

Thus, if a valid search summary has not been selected (block 221), an error message is presented to the user (block 22). Otherwise, detailed search results are obtained (block 223) and a search details page is built (block 224), and served to the Web browser 17. The routine then returns.

Figure 16:
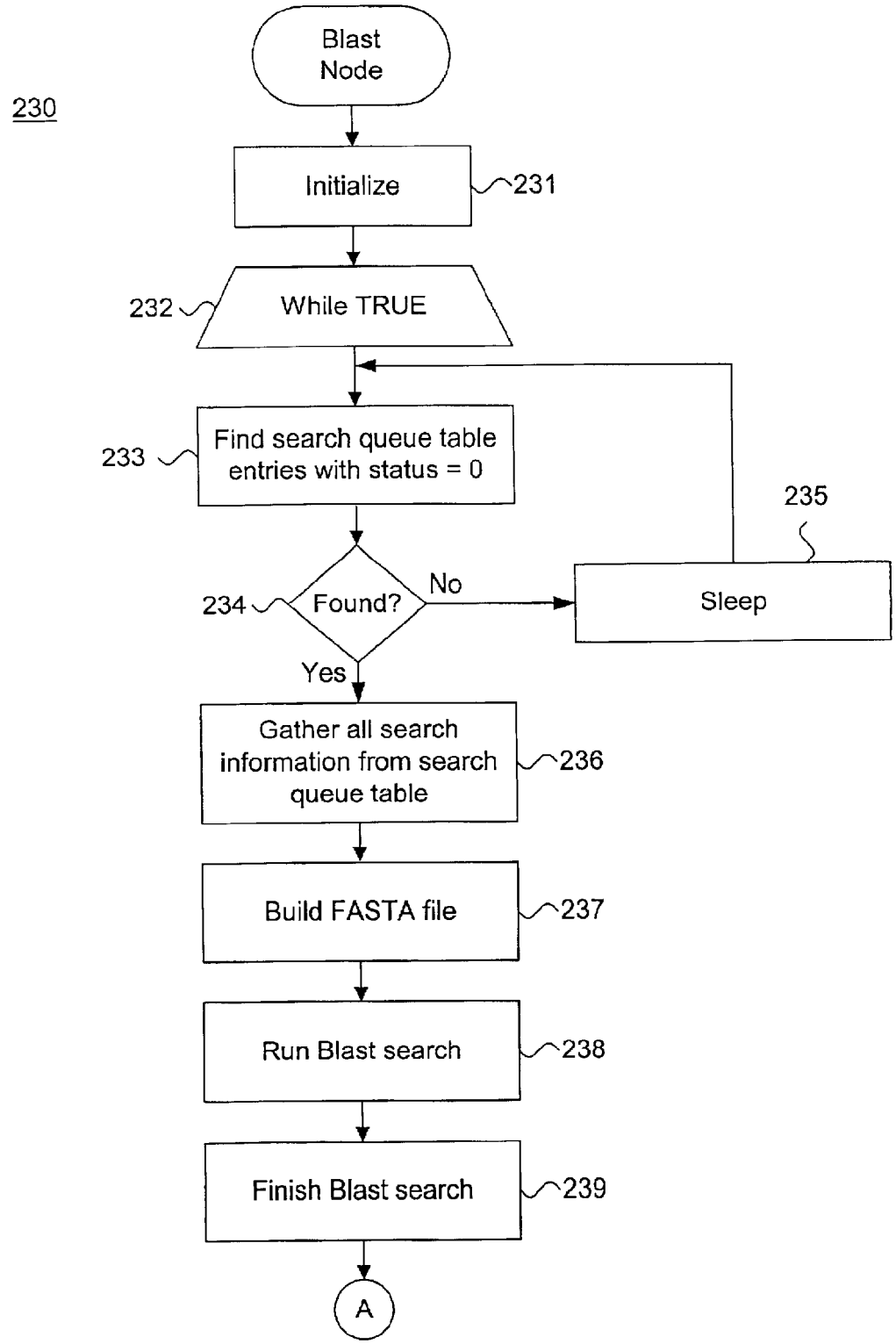
FIG. 16 is a flow diagram showing the Blast node (queue handler) which works in conjunction with the method of FIG. 9.

FIG. 16 is flow diagram showing the Blast node (queue handler) 230 which works in conjunction with the method 150 of FIG. 9. The purpose of this routine is to query the search queue 43 and to process search results into the search results table 44 in the relational database 33 at regular intervals. This routine operates in coordination with but independent from the Web server 17.

The Blast node 53 first begins by initializing (block 231) internal data structures and connections to the relational database 33 (shown in FIG. 2). The Blast node 53 then proceeds to process incoming search requests and completed search results in a continuous processing loop (blocks 232–244).

During each iteration (block 232), the Blast node 53 searches the search queue 43 (shown in FIG. 2) for those entries having a status equal to zero (block 233). A status of zero indicates that no search results are present. If no entries are found (block 234), the Blast node 53 sleeps for a pre-determined interval (block 235). In the described embodiment, an interval of 2,000 milliseconds is used, although other suitable intervals could also be used.

Once found (block 235), all search information is gathered from the search queue (block 236) and a file structured in the FASTA format is built (block 237) to store the input file for the Blast search. The search is then run (block 238) by sending each search request as a formatted database query command line containing relevant parameters and databases for execution by a Blast engine 54 (shown in FIG. 3).

The Blast node 53 waits for the Blast search to finish (block 239). Upon completion, the output of the Blast search is received as XML output from the Blast engine 54. This XML output is parsed (block 240) to allow the data to be reformatted to display search results for multiple sequence sets and multiple databases. The search results table 44 (shown in FIG. 3) is loaded with the parsed information (block 241) and the queue status is set to "Done" (block 242) indicating the search has completed. Execution of the routine 230 continues indefinitely (block 243) until the Blast node 53 is terminated.

While the invention has been particularly shown and described as referenced to the embodiments thereof, those skilled in the art will understand that the foregoing and other changes in form and detail may be made therein without departing from the spirit and scope of the invention.

What is claimed is:

1. A system for transacting a multi-sequence search against biological data repositories, comprising:

a user interface servlet receiving a set of search query parameters specifying a search request comprising a plurality of sequence sets for a plurality of sequence types and forwarding search results as sequences set information organized and reformatted for each sequence set;

a servlet engine parsing each sequence individually and determining each of the sequence types from the search query parameters, each sequence set encoding structured biological data values, and processing the search query parameters into a plurality of structured database queries comprising at least one structured database query for each sequence set according to the sequence types;

a database servlet loading a search queue with the structured database queries for each sequence set and identifying a biological data repository for each structured database query; and a queue handler launching individual search of the biological data repository identified for each structured database query for each sequence set and retrieving search results generated responsive to each such structured database query search.

2. A system according to claim 1, comprising:

a database engine interfaced to the database repository and executing each such structured database query identified for the structured database query.

3. A system according to claim 2, comprising:

an application programming interface exported from the database engine through which are exchanged each structured database query and the search results.

4. A system according to claim 1, comprising:

a search page built by the user interface servlet and specifying the search query parameters for the search request.

5. A system according to claim 1, comprising:

a search status page built by the user interface servlet and displaying a status of the search results.

6. A system according to claim 5, comprising:

a database servlet obtaining search information from the search results comprising at least one of a search name, a suer name, a search data, a sequence set and a database identifier and updating the search status page with the search information.

7. A system according to claim 1, comprising:

a search summary page built by the user interface servlet and displaying a summary of the search results.

8. A system according to claim 1, comprising:

a search graph page built by the user interface servlet and displaying a graphical summary of the search result similarities.

9. A system according to claim 8, wherein the search graph page further displays a sequence alignment between at least one such sequence set and a sequence set selected from the search results.

10. A system according to claim 1, comprising:

a search details page built by the user interface servlet and displaying the sequence set information for a select one of the search results.

11. A system according to claim 1, comprising:

a search page receiving as part of the search parameters at least one of a previously-entered sequence set and a new sequence set.

12. A system according to claim 1, comprising:

a formatted table receiving the search results and containing the sequence set information for each of the search results.

13. A system according to claim 1, comprising:

a database servlet providing at least one of adding, removing, formatting and creating a database storing sequence sets encoding biological data values.

14. A system according to claim 1, comprising:

a database servlet providing at least one of importing from and exporting to a file system sequence sets encoding biological data values.

15. A system according to claim 1, wherein the search parameters for the search request are selected from the group comprising at least one of a biological data repository, statistical search criteria, and a search type.

16. A method for transacting a multi-sequence search against biological data repositories, comprising:

receiving a set of search query parameters specifying a search request comprising a plurality of sequence sets for a plurality of sequence types;

parsing each sequence individually and determining each of the sequence types from the search query parameters, each sequence set encoding structured biological data values;

processing the search query parameters into a plurality of structured database queries comprising at least one structured database query for each sequence set according to the sequence types;

loading a search queue with the structured database queries for each sequence set and identifying a biological data repository for each structured database query;

launching individual search of the biological data repository identified for each structured database query for each sequence set;

retrieving search results generated responsive to each such structured database query search; and forwarding the search results as sequence set information organized and reformatted for each sequence.

17. A method according to claim 16, comprising:

executing each such structured database query using a database engine interface to the database repository identified for the structured database query.

18. A method according to claim 17, comprising:

exporting an application programming interface from the database engine through which are exchanged each structured database query and the search results.

19. A method according to claim 16, comprising:

building a search page specifying the search query parameters for the search request.

20. A method according to claim 16, comprising:

building a search status page displaying a status of the search results.

21. A method according to claim 20, comprising:

obtaining search information from the results comprising at least one of a search name, a user name, a search date, a sequence set and a database identifier; and updating the search status page with the search information.

22. A method according to claim 16, comprising:

building a search summary page displaying a summary of the search results.

23. A method according to claim 16, comprising:

building a search graph page displaying a graphical summary of the search result similarities.

24. A method according to claim 16, comprising:

building a search details page displaying the sequence set information for a select one of the search results.

25. A method according to claim 23, wherein the search graph page further displays a sequence alignment between at least one such sequence set and a sequence set selected from the search results.

26. A method according to claim 16, comprising:

receiving as part of the search parameters at least one of a previously-entered sequence set and a new sequence set.

27. A method according to claim 16, comprising:

receiving the search results as a formatted table containing the sequence set information for each of the search results.

28. A method according to claim 16, comprising:

providing at least one of adding, removing, formatting and creating a database storing sequence sets encoding biological data values.

29. A method according to claim 16, comprising:

providing at least one of importing from and exporting to a file system sequence sets encoding biological data values.

30. A method according to claim 16, wherein the search parameters for the search request are selected from the group comprising at least one of a biological data repository, statistical search criteria, and a search type.

31. A computer-readable storage medium holding code for performing the method according to claims 16, 17, 18, 19, 20, 21, 22, 23, 24, 25, 26, 27, 28, 29, or 30.

32. A system for accessing a plurality of biological data repositories using an extensible database access framework, comprising:

a user interface layer accepting search query parameters for and displaying search results from a search request for multiple sequence sets for a plurality of sequence types performed against a plurality of biological data repositories;

an intermediate layer processing the search request and the search results by interfacing with the user interface layer, comprising:

a servlet engine parsing each sequence individually and determining each of the sequence types from the search query parameters;

a user interface module processing the search query parameters into a plurality of structured database queries comprising at least one structured database query for each sequence set according to the sequence types and presenting database results as the formatted search results;

a database layer executing the structured database queries, comprising:

at least one queue handler loading the structured database queries, selecting a biological data repository for each structured database query, and retrieving the database results, each biological data repository containing sequence data stored into unstructured records which are each identified by a unique identifier; and at lease one database engine executing each structured database query against and obtaining the database results from each selected biological data repository.

33. A system according to claim 32, further comprising:

a status module providing a search progress status in the intermediate layer.

34. A system according to claim 32, further comprising:

a database module directly accessing the database engine in the intermediate layer by creating a database compatible with and retrieving individual sequence entries directly from the biological data repositories.

35. A system according to claim 32, comprising:

a set of servlets defined in the intermediate layer as server-executable program modules.

36. A system according to claim 32, comprising:

a search queue transiently storing each structured database query.

37. A system according to claim 32, comprising:

an application programming interface defined with the database engine through which the structured database query and the database results are communicated.

38. A system according to claim 32, comprising:

a database accessible in the intermediate layer referencing at least one of system information, search information and search results.

39. A system according to claim 32, comprising:

a plurality of queue handlers, each cooperatively assigning such a structured database query to at least one such database engine.

40. A system according to claim 39, comprising:

a control module prioritizing and scheduling execution of each such structured database query among the plurality of queue handlers.

41. A system according to claim 32, comprising:

a protocol stack exchanging the search query parameters and the search results between the user interface layer and the intermediate layer via HTML packets.

42. A system according to claim 32, wherein the biological data repositories comprise at least one of a client-based database, a server-based database and a network-based database.

43. A system according to claim 32, wherein the biological data comprises at least one of sequences of genome information for DNA and protein.

44. A method for accessing a plurality of biological data repositories using an extensible database access framework, comprising:
accepting search query parameters for and displaying search results from a search request for multiple sequence sets for a plurality of sequence types performed against a plurality of biological data repositories in a user interface layer;
processing the search request and the search results in an intermediate layer by interfacing with the user interface layer, comprising:
parsing each sequence individually and determining each of the sequence types from the search query parameters;
processing the search query parameters into a plurality of structured database queries comprising at least one structured database query for each sequence set according to the sequence types; and
presenting database results as the formatted search results;
executing the structured database queries in a database layer, comprising:
providing at least one queue handler loading the structured database queries, selecting a biological data repository for each structured database query, and retrieving the database results, each biological data repository containing sequence data stored into unstructured records which are each identified by a unique identifier; and
executing, via at least one database engine, each structured database query against and obtaining the database results from each selected biological data repository.

45. A method according to claim 44, further comprising:
providing a search progress status in the intermediate layer.

46. A method according to claim 44, further comprising:
directly accessing the database engine in the intermediate layer by creating a database compatible with and retrieving individual sequence entries directly from the biological data repositories.

47. A method according to claim 44, comprising:
defining a set of servlets in the intermediate layer as server-executable program modules.

48. A method according to claim 44, comprising:
maintaining a search queue transiently storing each structured database query.

49. A method according to claim 44, comprising:
defining an application programming interface with the database engine through which the structured database query and the database results are communicated.

50. A method according to claim 44, comprising:
referencing at least one of system information, search information and search results stored in a database accessible in the intermediate layer.

51. A method according to claim 44, comprising:
providing a plurality of queue handlers, each cooperatively assigning such a structured database query to at least one such database engine.

52. A method according to claim 51, comprising:
prioritizing and scheduling execution of each such structured database query among the plurality of queue handlers.

53. A method according to claim 44, comprising:
exchanging the search query parameters and the search results between the user interface layer and the intermediate layer via HTML packets.

54. A method according to claim 44, wherein the biological data repositories comprise at least one of a client-based database, a server-based database and a network-based database.

55. A method according to claim 44, wherein the biological data comprises at least one of sequences of genome information for DNA and protein.

56. A computer-readable storage medium holding code for performing the method according to claims 44, 45, 46, 47, 48, 49, 50, 51, 52, 53, 54, or 55.

57. A system for providing flexible access and retrieval of sequence data from a plurality of biological data repositories, comprising:
a plurality of biological data repositories, each data repository containing sequence data stored into structured records uniquely identified;
a queue handler interfacing to each data repository by dynamically locating and selecting at least one such biological data repository for a plurality of search queries and launching one such search query against each selected biological data repository; and
a user interface accepting search query parameters from a user specifying a search request comprising the search queries for a plurality of sequence sets for a plurality of sequence types and presenting results obtained from a search engine as ordered tables of search results.

58. A system according to claim 57, comprising:
a user interface servlet parsing the query parameters received from a user into a sequence data search string.

59. A system according to claim 57, comprising:
a database servlet parsing the search results obtained by the search engine based on sequence set.

60. A method for providing flexible access and retrieval of sequence data from a plurality of biological data repositories, comprising:
maintaining a plurality of biological data repositories, each data repository containing sequence data stored into structured records uniquely identified;
interfacing to each data repository through a queue handler dynamically locating and selecting at least one such biological data repository for a plurality of search queries and launching one such search query against each selected biological data repository; and
accepting search query parameters from a user specifying a search request comprising the search queries for a plurality of sequence sets for a plurality of sequence types and presenting results obtained from a search engine as ordered tables of search results.

61. A method according to claim 60, comprising:
parsing the query parameters received from a user into a sequence data search string.

62. A method according to claim 60, comprising:
parsing the search results obtained by the search engine based on sequence set.

63. A computer-readable storage medium holding code for performing the method according to claims 60, 61, or 62.

* * * * *